(12) United States Patent
Rosholm et al.

(10) Patent No.: US 6,763,257 B1
(45) Date of Patent: Jul. 13, 2004

(54) METHOD OF ESTIMATING THE BMD OF A BONE USING RADIOGRAMMETRY

(75) Inventors: Anders Rosholm, Hellerup (DK); Hans Henrik Thodberg, Holte (DK)

(73) Assignee: Sectra A/S, Roskilde (DK)

( * ) Notice: Subject to any disclaimer, the term of this patent is extended or adjusted under 35 U.S.C. 154(b) by 0 days.

(21) Appl. No.: 09/959,114

(22) PCT Filed: Apr. 17, 2000

(86) PCT No.: PCT/DK00/00194

§ 371 (c)(1),
(2), (4) Date: Dec. 4, 2001

(87) PCT Pub. No.: WO00/62673

PCT Pub. Date: Oct. 26, 2000

(30) Foreign Application Priority Data

Apr. 20, 1999 (DK) .......................................... 19900531

(51) Int. Cl.[7] .................................................. A61B 5/05
(52) U.S. Cl. ..................................................... 600/407
(58) Field of Search ................................ 600/300, 407; 378/4, 21, 62, 64; 250/363.02, 363.04, 363.09

(56) References Cited

U.S. PATENT DOCUMENTS 4,721,112 A    1/1988  Hirano et al.

FOREIGN PATENT DOCUMENTS

EP    0 570 936 A    11/1993

OTHER PUBLICATIONS

Mirsky et al. "Current concepts review: Bone densitometry in orthopaedic practice", Journal of Bone and Joint Surgery, (Nov. 1998) vol. 80.*

Zamberlan et al. "Evaluation of cortical thickness and bone density by roentgen microdensitometry in growing males and females", Imaging Techniques (1996), vol. 155.*

Tothill, "Methods of bone mineral measurement," Physics In Medicine and Biology, vol. 34, No. 5, 1989, pp. 543–572, Great Britain.

Bailey et al., "Computer–assisted measurement of cortical bone," Proceedings of the 1978 IEEE National Aerospace and Electronics Conference, vol. 1, May 1978, pp. 393–397, United States.

"Computerised Radiogrammetric Measurements in Digitised Forearm Radiographs," Poster, Displayed at the European Congress on Osteoporosis, Sep. 11–15, 1998, Berlin, Germany.

Lindsay et al., "Osteoporosis International," The Second International Conference on Osteoporosis, p. 14, Nov. 13–16, 1997, Osaka, Japan.

Lindsay et al., "Osteoporosis International," European Congress on Osteoporosis, p. 68, Sep. 11–15, 1998, Berlin, Germany.

* cited by examiner

Primary Examiner—Ali Imam
(74) Attorney, Agent, or Firm—Birch, Stewart, Kolasch & Birch, LLP

(57) ABSTRACT

A method for estimating the bone quality or skeletal status of a vertebrate on the basis of two-dimensional image data comprising information relating to the cortical bone of at least a part of a bone of the vertebrate, the image data being data obtained by exposing at least the part of the bone to electromagnetic radiation, the method comprising estimating the bone quality or skeletal status on the basis of a a grey value difference between oblong density variations in the image data and other parts of the image data. These oblong density variations may be caused by osteoporosis, osteopenia or hyperparathyroidism or other bone disorders is called "intra cortical resorption", "periosteal resorption", "endosteal resorption", "striation", "scalloping", or "spongiosation".

15 Claims, 3 Drawing Sheets

METHOD OF ESTIMATING THE BMD OF A BONE USING RADIOGRAMMETRY

FIELD OF THE INVENTION

The present invention relates to a method of estimating the BMD of a bone by using radiogrammetry.

DESCRIPTION OF THE BACKGROUND ART

Today, Bone Mineral Density (BMD) is most often estimated using Dual X-ray Absorptiometry (DEXA) where two images are taken at two different X-ray energies and where BMD is derived from the image resulting from a subtraction of the two images. It is also possible to estimate BMD using Radiographic Absorptiometry (RA), where the X-ray absorption in the bone is used for determining the BMD of the bone. However, the use of that method requires the use of a calibration wedge in order to determine what grey level in the image corresponds to which thickness of e.g. Aluminium. This is required in order to take into account differences in film type, developing methods, radiation doses, and radiation energy used.

The use of this calibration wedge, though, incorporates the disadvantage that forgetting it or using the wrong wedge will render the image data totally useless, where after the patient will have to be irradiated once again.

BRIEF SUMMARY OF THE INVENTION

It is an object of the invention to provide a method of using standard X-ray images for providing BMD data without having to introduce standard wedges or other elements for use in the calculation.

The present invention relates to the use of values normally derived in radiogrammetry. Until now, radiogrammetry has mainly been used for more coarse predictions, such as predictions of fracture risk and the like. These types of predictions merely relate to the determination of whether a derived value is below or above a given threshold value. Exactly how the derived value generally correlates with e.g. BMD has not been in focus and has not been important, as long as the correlation in the vicinity of the threshold value is acceptable.

In radiogrammetry, the usual manner is to start out with an X-ray image of the bone and therefrom determine the overall width, w, of the bone and either the thickness, t, of the cortical shell of the bone, or the inner width, $w_i$, of the bone. Obviously, $w=2t+w_i$.

As seen in "Bone Densitometry and Osteoporosis", H. K. Genant, G. Guglielmi and M. Jergas, Springer, 1998, chapter 14, different manners have been used in the estimation of e.g. the fracture risk of a bone:

the combined cortical thickness (CCT): $w-w_i \propto t$,
the cortical index: $(w-w_i)/w \propto t/w$,
the cortical area: $w^2-w_i^2 \propto t(w-t)$, and
the relative cortical area: $(w^2-w_i^2)/w^2 \propto (t/w)\times(1-t/w)$.

However, as has also been acknowledged by the prior art, these values have been found to correlate moderately at best with BMD measured using e.g. DEXA.

It is an object of the present invention to provide a novel manner of estimating the BMD of a bone—a manner in which a standard X-ray image may be used and a standard manner of deriving t, w, and/or $w_i$, may be used, but which has been found to correlate better with e.g. a DEXA-BMD measurement of the bone.

Thus, in a first aspect, the invention relates to a method for estimating the Bone Mineral Density (BMD) of a bone, the method comprising:

obtaining two-dimensional image data comprising information relating to the cortical bone of at least a part of the bone, the image data being data obtained by exposing at least the part of the bone to electromagnetic radiation, determining a thickness, t, of the cortical bone,
estimating the BMD of the bone as:

$$BMD = \text{const.}_A \times t,$$

where $\text{const.}_A$ is determined from a calibration based on values of t and corresponding BMD values for one or more bones.

In the present context, we will denote BMD determined using the method of the invention DXR-BMD.

In the present context, $\text{const.}_A$ may be a constant value used for e.g. a specific bone (typically of a predetermined type and a predetermined part thereof but for all persons in a predetermined group of persons, such as all Caucasian women.

A major reason for the existence of $\text{const.}_A$ with those properties is that it has been found that a number of bones in the human vertebrate have very similar shapes—except perhaps for a scaling factor—for large groups of persons, such as all Caucasian women. This means that across a predetermined group of persons, no geometric factor needs to be taken into account in order to adapt the measurement across the group.

It is contemplated that a different value for $\text{const.}_A$ will be suitable for e.g. Asian women or Caucasian men.

Also, it has been found that the density of non-porous bone is surprisingly constant. Or rather, the natural porosity of the dense bone is quite constant. This is also a reason why the same $\text{const.}_A$ may be used for a whole group of persons. However, it has been found that the natural porosity of bone varies slightly with age. Thus, in order to obtain an even better BMD measure, it may be desired to have $\text{const.}_A$ depend on a porosity determined from the image data.

On the other hand, there are factors which relate to the individual person and which are quite useful in a determination of BMD. Factors of these types are age, ethnicity and sex. As to ethnicity and sex, different $\text{const.}_A$'s may be provided for different ethnicities and sexes—or an expression for $\text{const.}_A$ may be provided which depends on these values and is thus adapted to take that into account. As to age, entering the age and in that manner taking the variation of bone porosity with age into account will provide this correction without requiring determination of porosity from the image data.

In these situations, the values or expressions for $\text{const.}_A$ may be derived on the basis of the values of t and corresponding BMD values for one or more bones as well as information relating to one or more of the factors—where the factors are those relating to the person having one of the one or more bones.

Preferably, $\text{const.}_A$ will not depend on any other measure derived from the image data.

A scaling factor derives from different distances from an X-ray source to the bone and from the bone to an image forming means, such as a CCD and an X-ray film. Thus, before deriving t, the image data may be scaled. This scaling may be considered a normalisation of the image data.

In order to obtain a suitable reproducibility, it is preferred that the method comprises:

determining a direction at least substantially perpendicular to a longitudinal axis of the bone, determining the thickness, t, of the cortical bone along the direction.

In one situation, t may be determined along a single line extending in the direction.

If a better reproducibility of the determination is desired, values of t may be determined for a plurality of lines extending in the direction and being positioned at different positions along the longitudinal direction of the bone, and the BMD may be determined on the basis of t values corresponding to the individual lines. In that situation, the BMD may be determined as: $const._A$ times a mean value of the t values corresponding to the individual lines.

In the above, first aspect, the correlation with t has been found sufficient especially when t is small. However, a second order correction of $t^2/w$ has been found to make the BMD determination better for larger values of t.

Thus, in a second aspect, the invention relates to a method for estimating the Bone Mineral Density (BMD) of a bone, the method comprising:

obtaining two-dimensional image data comprising information relating to the cortical bone of at least a part of the bone, the image data being data obtained by exposing at least the part of the bone to electromagnetic radiation, determining a thickness, t, of the cortical bone, determining an overall width, w, of the bone, estimating the BMD of the bone as:

$$BMD = const._B \times t(1-t/w),$$

where $const._B$ is determined from a calibration where pairs of (t,w) have been calibrated to corresponding BMD values for one or more bones.

The above considerations relating to $const._A$ will also apply to $const._B$.

Also, in order to increase the reproducibility, the method preferably comprises:

determining a direction at least substantially perpendicular to a longitudinal axis of the bone, determining a thickness, t, of the cortical bone along the direction determining an overall width, w, of the bone along the direction.

Again, in one situation, t and w may be determined along a single line extending in the direction.

If a better reproducibility of the determination is desired, pairs of (t,w) may be determined for a plurality of lines extending in the direction and being positioned at different positions along the longitudinal direction of the bone, and the BMD may be determined on the basis of pairs of (t,w) corresponding to the individual lines. In that situation, the BMD may be determined on the basis of mean values of the t and w values corresponding to the individual lines.

In any of the aspects of the invention, the reproducibility may be increased by determining a number of t values, and, for the second aspect, w values, for the same bone and at different positions of the bone, whereby, preferably, t values, and, for the second aspect, w values, are determined for each of more than 10, such as more than 20, such as more than 40, such as more than 60, such as more than 80, such as more than 100, such as more than 110 lines per cm. of the bone and within a predetermined longitudinal part of the bone.

It has been found that measurements from a number of bones, such as the metacarpals and radius/ulna, increase the reproducibility of the BMD determination.

Virtually any tubular bone may be used in the aspects of the present invention. Presently, it has been found that suitable bones are selected from the group consisting of: radius, ulna, tibia, fibula, metacarpal, phalanges and femur.

In the present context, the radiation is preferably X-ray radiation, and the image data are either directly obtained using a CCD or is digital data representing a scanned X-ray image obtained using X-ray film.

When the image data is scanned from an X-ray film, this may be from an X-ray film having a resolution of at least 1 pair of lines per centimetre, such as at least 2 pairs of lines per mm, preferably at least 3 pairs of lines per mm, such as at least 4 pairs of lines per mm, preferably at least 5 pairs of lines per mm, such as at least 6 pairs of lines per mm, such as at least 7 pairs of lines per mm, preferably at least 9 pairs of lines per mm, such as at least 10 pairs of lines per mm.

The scanning may be performed at a resolution of at least 10 lines per cm, such as at least 25 lines per cm, preferably at least 100 lines per cm, such as at least 200 lines per cm, such as at least 250 lines per cm.

Some types of tubular bones may be equally well suited for radiogrammetric measurement around their circumferences. This is the case for the metacarpals. However, this is not the case for all tubular bones, such as for the radius and ulnar. These bones are circularly shaped at the sides thereof pointing away from each other. The sides thereof pointing toward each other, however, are wing-shaped and less suitable for a precise determination of t.

Thus, when the bone is a radius, it is preferred that the t value or values is/are determined on a radial side of the radius, and when the bone is an ulnar, it is preferred the t value or values is/are determined on an ulnar side of the ulnar.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, a description is given of the product Pronosco X-posure System™ that incorporates a preferred embodiment of the invention and with reference to the drawings which are given by way of illustration only, and thus are not limitative of the present invention, and wherein.

DETAILED DESCRIPTION OF THE INVENTION

Theoretical Considerations Concerning BMD from Radiogrammetry

To define BMD in the context of e.g. a DEXA machine, one projects the bone onto a plane. In this projection, one defines a certain region or area of the bone. BMD is defined as the mineral mass of the bone projected onto this area, divided by the area itself:

$$BMD = \text{Bone Mineral Mass/Area}$$

The mass used is the ash weight, i.e. the mineral content, which is mainly constituted by Calcium. The unit of BMD is $g/cm^2$ or $mg/cm^2$.

When defining the area, care must be taken to understand the projection geometry. In the case of X-ray images and fan-beam mode of DEXA machines, there is a certain magnification M of the distances in the image of the bone. This magnification is dictated by the distance $D_{sf}$ from the X-ray emitting spot to the film and the distance $D_{of}$ from the object to the film according to the following relation:

$$M = \frac{1}{1 - D_{of}/D_{sf}}$$

This factor, M, is incorporated in the const-values used for the determination of DXR-BMD according to the invention.

The X-ray images for the X-posure System™ are acquired with a nominal spot-film distance $D_{sf}=100$ cm. The hand rests directly on the film cassette, and this gives a distance $D_{of}$ in the range 1–5 cm. A change of spot-film distance of 10 cm gives a change in M of 0.3% (assuming $D_{of}=3$ cm). A change of object-film distance of 2 cm (e.g. by lifting the hand from the film) gives a change in M of 2%. Hence it is much more important to control the object-film distance than the spot-film distance. This is reflected in the user manual for the system.

DEXA bone densitometers utilise absorptiometry to estimate the BMD. These devices measure the reduction of the intensity of X-rays as they pass though the tissue. This is also true for Radiographic Absorptiometry (RA).

In contrast, the Pronosco X-posure System™ does not use the intensities of the image in a quantitative manner. This would require the presence of e.g. an aluminium wedge in every radiograph, as used in RA-systems.

Instead, the Pronosco X-posure System™ bases its measurement on radiogrammetry. Radiogrammetry is the measurement of distances on the film.

The following sections describe the radiogrammetry and the texture analysis.

Radiogrammetry and Bone Volume Per Area (VPA)

The Pronosco X-posure System™ determines the cortical bone volume using radiogrammetry.

The bone volume per area is denoted VPA. For a cylindrical bone, the following exact formula can be derived:

$$VPA = \pi * t * (1 - t/W)$$

Figure 1:
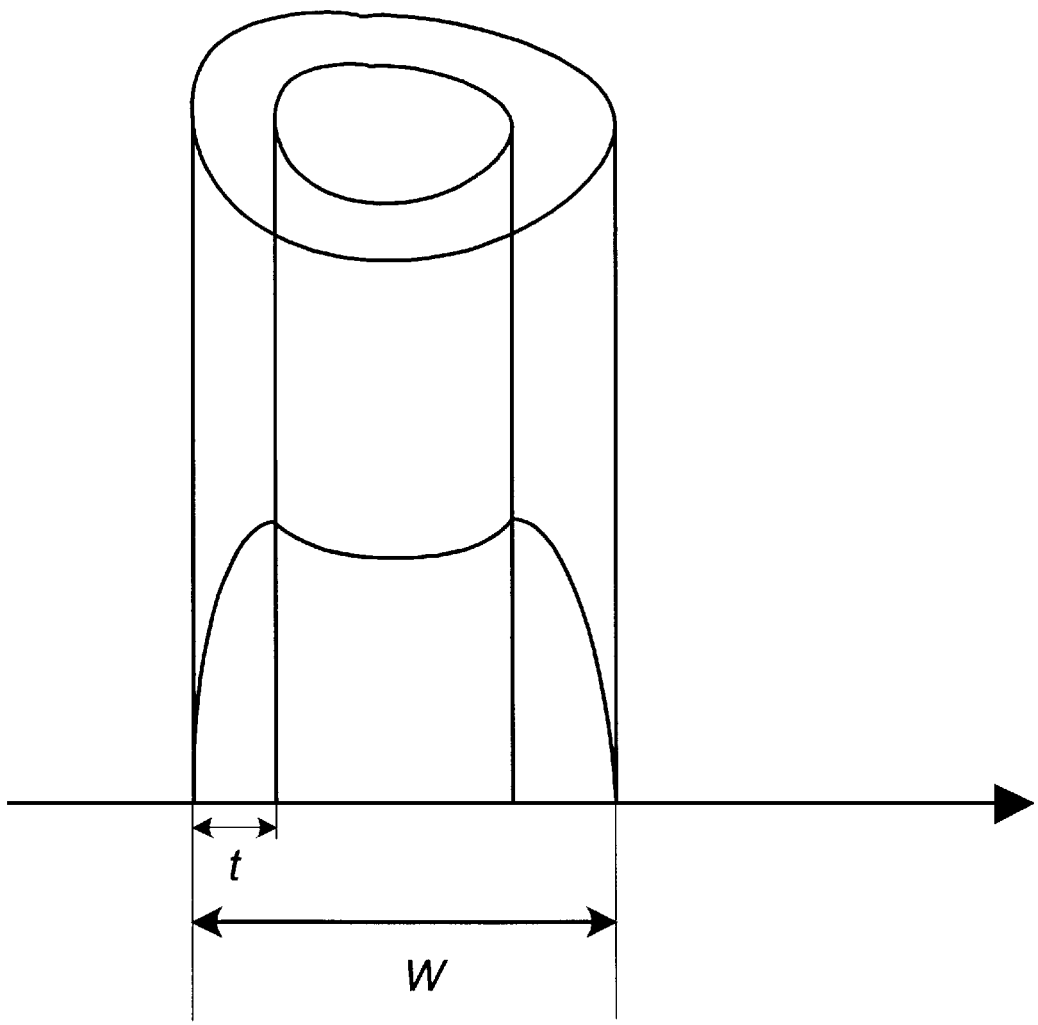
FIG. 1 illustrates the cortical thickness t and the bone width W. Shown is a cross section of a cortical bone and the thickness profile of the bone when projected onto the film. The projection shows a characteristic shape with local maxima at the boundaries of the medullar region (at the endosteal surface).

Here W is the diameter of the bone and t is the cortical thickness, as illustrated in FIG. 1. If the bone is not cylindrical, the factor $\pi$ is replaced by a geometrical factor f.

$$VPA = f * t * (1 - t/W)$$

The factor f depends on the shape of the bone. It can be assumed that the cross sectional shape of bones for the population covered by the BMD formula (Caucasian women) is invariant to a good approximation, i.e. that only the cortical thicknesses and the overall sizes vary, while the general shape is constant. With this assumption, the factor f is a constant. This assumption is eventually verified by the high correlation between DXR-BMD and DEXA-BMD demonstrated in the clinical trials.

The bone volume is used to compute the BMD estimate.

$$BMD = c * VPA$$

This relation states that the bone volume is proportional to the bone mass. This is based on the assumption that cortical bone tissue has a constant mineral content per unit volume. This assumption is eventually verified in the high correlation between DXR-BMD and DEXA-BMD demonstrated in the clinical trials.

If, however, porosity of the bone is desired taken into account, c could be replaced by $c \times (1-p)$ where p is a measure of porosity determined from the image data. Otherwise, age may be introduced, as age and porosity in the dense bone has been found to correlate.

The Measurement Region for VPA

Figure 2:
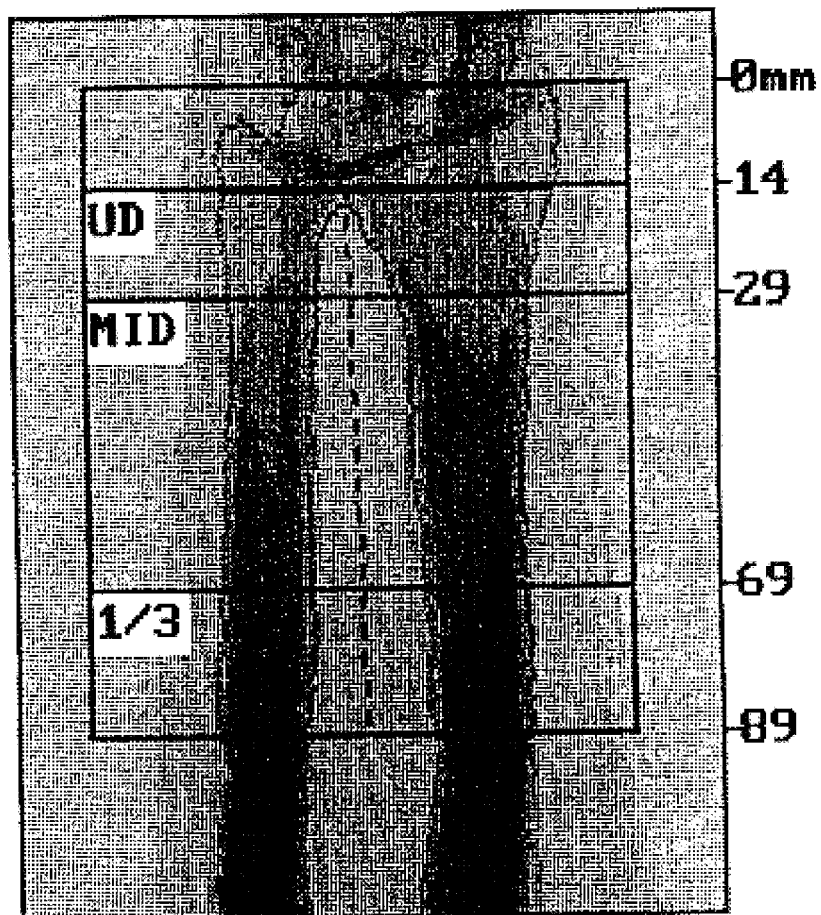
FIG. 2 illustrates the regions used in a Hologic QDR 2000 DEXA apparatus as made by Hologic, USA. The MID region starts 15 mm below the lower edge of the radius end plate. The bottom of the MID region is defined as 10 mm above the location of the middle of the ⅓ region. The ⅓ region in turn is defined using information about the length of the forearm. See the Hologic Manual in Appendix F for a complete description of the Hologic definition of the MID.

The DEXA apparatus uses the region MID shown in FIG. 2.

Figure 3:
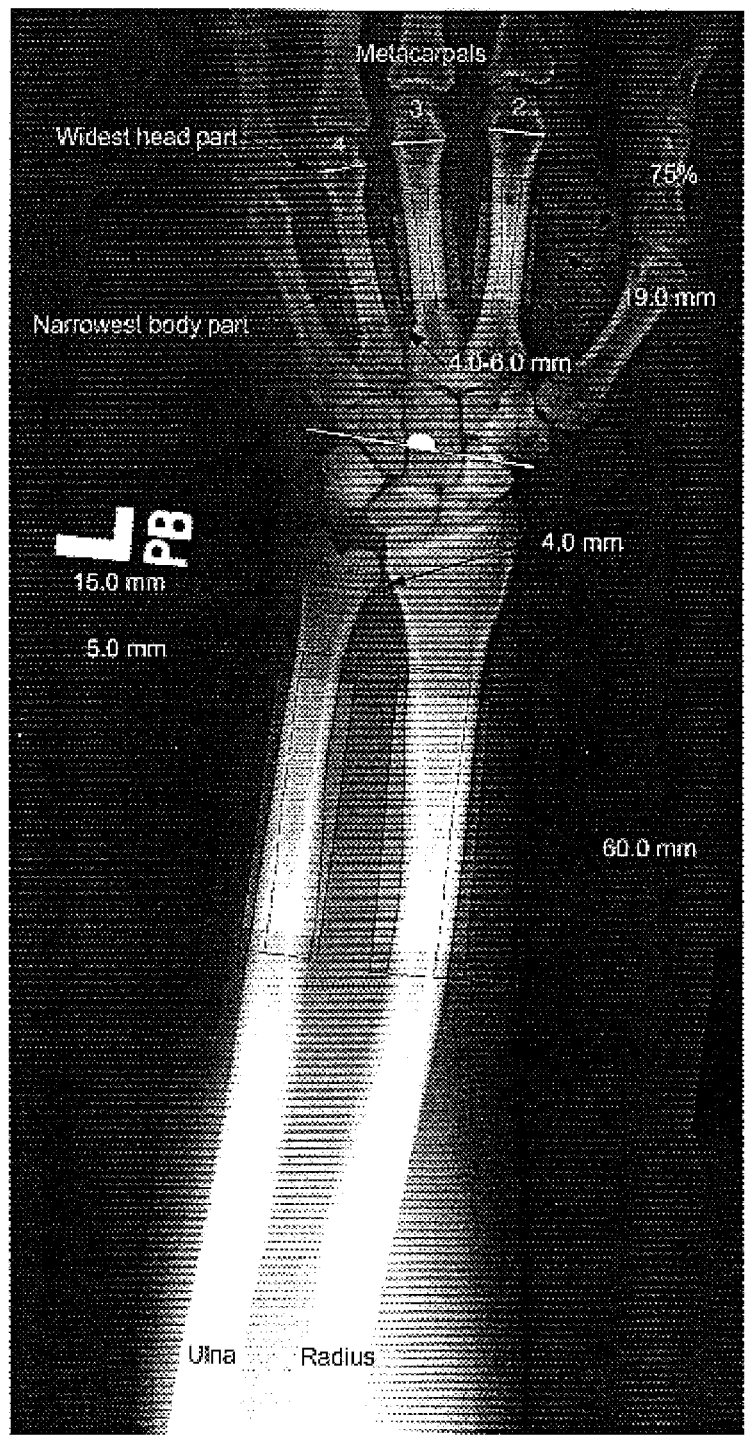
FIG. 3 illustrates the regions of interest used in the Pronosco X-posure System™ embodying the present invention. Comparing with FIG. 2, it is seen that the ROIs in the radius and ulna are similar—but not identical—to the regions used in the DEXA apparatus. In the metacarpals, the cortical thicknesses are determined on both sides (radial and ulnar sides), while in the radius and ulna, only the radial and ulnar sides, respectively, are determined.

Both the DXR-BMD and the DEXA-BMD are estimates of the true BMD in the MID region. DXR-BMD arrives at this estimate using information from several bone regions. These regions are shown in FIG. 3.

The VPA used in DXR-BMD is computed as an average of VPAs computed in the five bones according to the formulae $$VPA = \tfrac{1}{2} VPA_{radius/ulna} + \tfrac{1}{2} VPA_{met}$$

$$VPA_{met} = \tfrac{1}{3}(VPA_{met2} + VPA_{met3} + VPA_{met4})$$

$$VPA_{radius/ulna} = \frac{1}{2}(VPA_{radius} + VPA_{ulna})$$

$$VPA = \pi * t * (1 - t/W)$$

VPA is the bone volume per area and is computed from the average cortical thickness t and the outer diameter W of the bone. VPA has the dimension mm. For the metacarpals t is the average of the thicknesses in the two sides, while for radius and ulna only the outer sides are used. The axial aspects of radius and ulna protrude wing-shaped into the interosseous space to anchor the interosseous membrane.

In comparison with traditional radiogrammetry, the Pronosco X-posure System™ utilises the automation and computing power of modern PCs to compound measurements from a very large number of points along the bones to yield an average cortical thickness for a given region of a given bone. The Pronosco X-posure System™ measures the cortical thickness at 118 points per centimetre along the axis of a bone, which adds to the reproducibility and accuracy of the BMD estimate.

The use of radiogrammetry in the metacarpals to estimate the BMD in the forearm is based on the high correlation between BMD in these bones. The same applies to the use of a slightly different ROI in the radius and ulna as compared to the ROI in the predicate device. It should be noted that the ROI's in ulna and radius are positioned identically with respect to distances from the 4.0 mm landmark.

In fact, presently, a correlation of 0.90 has been found between the present invention and DEXA-BMD when using the formula according to the second aspect of the invention and as described with respect to the drawings.

When using the more coarse equation using merely t from the image data, a correlation of 0.88 is seen between DXR-BMD and DEXA-BMD.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for estimating the Bone Mineral Density (BMD) of a bone, the method comprising:

obtaining two-dimensional image data comprising information relating to the cortical bone of at least a part of the bone, the image data being data obtained by exposing at least the part of the bone to electromagnetic radiation, determining a thickness, t, of the cortical bone, determining an overall width, w, of the bone, estimating the BMD of the bone as:

$$BMD = \text{const.}_B \times t(1 - t/w),$$

where $\text{const.}_B$ is determined from a calibration where pairs of (t,w) have been calibrated to corresponding BMD values for one or more bones.

2. The method according to claim 1, the method comprising:

determining a direction at least substantially perpendicular to a longitudinal axis of the bone, determining a thickness, t, of the cortical bone along the direction, determining an overall width, w, of the bone along the direction.

3. The method according to claim 2, wherein t and w are determined along a single line extending in the direction.

4. The method according to claim 2, wherein pairs of (t,w) are determined for a plurality of individual lines extending in the direction and being positioned at different positions along the longitudinal direction of the bone, and wherein the BMD is determined on the basis of pairs of (t,w) corresponding to the individual lines.

5. The method according to claim 4, wherein the BMD is determined on the basis of mean values of the t and w values corresponding to the individual lines.

6. The method according to claim 4, wherein t and w values are determine for each of more than 10 lines per cm. of the bone within a predetermined longitudinal part of the bone.

7. The method according to claim 4, wherein t and w values are determined for each of more than 20 lines per cm of the bone within a predetermined longitudinal part of the bone.

8. The method according to claim 4, wherein t and w values are determined for each of more than 40 lines per cm of the bone within a predetermined longitudinal part of the bone.

9. The method according to claim 4, wherein t and w values are determined for each of more than 60 lines per cm of the bone within a predetermined longitudinal part of the bone.

10. The method according to claim 4, wherein t and w values are determined for each of more than 80 lines per cm of the bone within a predetermined longitudinal part of the bone.

11. The method according to claim 4, wherein t and w values are determined for each of more than 100 lines per cm of the bone within a predetermined longitudinal part of the bone.

12. The method according to claim 4, wherein t and w values are determined for each of more than 110 lines per cm of the bone within a predetermined longitudinal part of the bone.

13. The method according to claim 1, wherein the bone is a tubular bone chosen from the group consisting of radius, ulna, tibia, fibula, metacarpal, phalanges and femur.

14. The method according to claim 13, wherein the bone is a radius, and wherein the t value or values is/are determined on a radial side of the radius.

15. The method according to claim 13, wherein the bone is an ulnar, and wherein the t value or values is/are determined on an ulnar side of the ulnar.

* * * * *